United States Patent
Savagian et al.

(10) Patent No.: US 9,247,915 B2
(45) Date of Patent: Feb. 2, 2016

(54) MICROFIBER RADIOGRAPHY COMFORT DEVICE

(71) Applicant: Brady Worldwide, Inc., Milwaukee, WI (US)

(72) Inventors: Michael Savagian, Bryant, WI (US); Andrew Schmitt, Shorewood, WI (US)

(73) Assignee: Brady Worldwide, Inc., Milwaukee, WI (US)

( * ) Notice: Subject to any disclaimer, the term of this patent is extended or adjusted under 35 U.S.C. 154(b) by 16 days.

(21) Appl. No.: 14/197,434

(22) Filed: Mar. 5, 2014

(65) Prior Publication Data

US 2015/0250432 A1   Sep. 10, 2015

(51) Int. Cl.
*A61B 6/04*  (2006.01)
*A61B 6/00*  (2006.01)
(Continued)

(52) U.S. Cl.
CPC ............ *A61B 6/04* (2013.01); *A61B 5/0091* (2013.01); *A61B 6/0407* (2013.01); *A61B 6/502* (2013.01);
(Continued)

(58) Field of Classification Search
CPC ........ A61B 6/0407; A61B 6/502; A61B 6/04; A61B 6/4291; A61B 6/544; A61B 5/4312; A61B 2019/205; A61B 5/05; A61B 5/0507; A61B 5/7257; A61B 6/032; A61B 8/0825; A61B 8/14; A61B 8/15; A61B 8/406; A61B 8/4209; A61B 8/4483; A61B 8/485; A61B 19/02; A61B 19/081; A61B 19/088; A61B 5/0091; A61B 8/403; A61B 2562/14; A61B 19/54; A61B 2019/5454; A61B 2019/5466; A61B 2019/5495; B32B 2250/44; B32B 2262/0253; B32B 2262/0276; B32B 2262/0292; B32B 2307/20; B32B 2307/748; B32B 2535/00; B32B 27/12; C08K 5/52; C08K 5/09; C08K 5/55; B29C 33/60; C02F 1/56; C08L 75/00

USPC .................................................. 378/37, 208
See application file for complete search history.

(56) References Cited

U.S. PATENT DOCUMENTS

| 5,185,776 A | 2/1993 | Townsend |
| 5,311,883 A | 5/1994 | Sherman |

(Continued)

FOREIGN PATENT DOCUMENTS

| AU | 2008201638 A1 | 5/2008 |
| WO | 2006050466 A1 | 5/2006 |

OTHER PUBLICATIONS

Dibble, et al., Mammography with Breast Cushions, Women's Health Issues, 2005, 15:55-63.

(Continued)

*Primary Examiner* — Irakli Kiknadze
(74) *Attorney, Agent, or Firm* — Quarles & Brady LLP

(57) ABSTRACT

A radiography comfort device may be selectively attached to a panel of a medical imaging device. The radiography comfort device includes a woven microfiber fabric and a first adhesive that are both radiolucent. The woven microfiber fabric has a first surface and a second surface on opposing sides of the woven microfiber fabric. The first adhesive is laminated to the second surface of the woven microfiber fabric. When the radiography comfort device is attached to the panel of the medical imaging device using the first adhesive, the first surface of woven microfiber fabric is presented for contact by tissue of an individual being imaged. Further, a pad can be laminated to a portion of the periphery of the fabric to provide an edge cushion when the comfort device is attached to the panel.

20 Claims, 4 Drawing Sheets

(51) Int. Cl.
*A61B 8/00* (2006.01)
*A61B 5/00* (2006.01)
*A61B 19/02* (2006.01)
*B32B 5/02* (2006.01)
*B32B 5/24* (2006.01)
*B32B 7/06* (2006.01)
*B32B 7/12* (2006.01)
*B32B 27/12* (2006.01)
*B32B 3/08* (2006.01)
*A61B 19/08* (2006.01)

(52) U.S. Cl.
CPC ............ *A61B 8/403* (2013.01); *A61B 19/02* (2013.01); *A61B 19/088* (2013.01); *B32B 3/08* (2013.01); *B32B 5/024* (2013.01); *B32B 5/245* (2013.01); *B32B 7/06* (2013.01); *B32B 7/12* (2013.01); *B32B 27/12* (2013.01); *A61B 19/081* (2013.01); *B32B 2250/44* (2013.01); *B32B 2262/0253* (2013.01); *B32B 2262/0276* (2013.01); *B32B 2262/0292* (2013.01); *B32B 2307/20* (2013.01); *B32B 2307/748* (2013.01); *B32B 2535/00* (2013.01)

(56) References Cited

U.S. PATENT DOCUMENTS

| | | | |
|---|---|---|---|
| 5,541,972 | A | 7/1996 | Anthony |
| 6,418,188 | B1* | 7/2002 | Broadnax ............ 378/37 |
| 6,577,702 | B1 | 6/2003 | Lebovic et al. |
| 6,765,984 | B2 | 7/2004 | Higgins et al. |
| 6,850,590 | B2 | 2/2005 | Galkin |
| 6,968,033 | B2 | 11/2005 | Lebovic et al. |
| 6,975,701 | B2 | 12/2005 | Galkin |
| 7,142,631 | B2 | 11/2006 | Galkin |
| 7,502,441 | B2 | 3/2009 | Lebovic et al. |
| 7,505,555 | B2* | 3/2009 | Hermann ............ A61B 6/0414 378/210 |
| 7,616,732 | B2 | 11/2009 | Lebovic et al. |
| 8,098,793 | B2 | 1/2012 | Lebovic et al. |
| 8,401,145 | B1 | 3/2013 | Boutte et al. |
| 2005/0059877 | A1* | 3/2005 | Falbo ............ 600/407 |
| 2012/0033786 | A1 | 2/2012 | Shafer et al. |
| 2013/0066288 | A1* | 3/2013 | Lin ............ 604/360 |

OTHER PUBLICATIONS

Davey, Pain During Mammography: Possible Risk Factors and Ways to Alleviate Pain, Radiography, 2007, 13:229-234.
Sapir, et al., Does Mammography Hurt?, Journal of Pain and Symptom Management, 2003, 25(1):53-63.
Poulos, et al., Mammography Discomfort: A Holistic Perspective Derived from Women's Experiences, Radiography, 2005, 11:17-25.
Robinson, et al., The Power and the Pain: Mammographic Compression Research from the Service-Users' Perspective, Radiography, 2013, 19:190-195.
Whelehan, et al., The Effect of Mammography Pain on Repeat Participation in Breast Cancer Screening: A Systematic Review, The Breast, 2013, 22:389-394.
Beekley Corporation, Bella Blankets Protective Coverlets for Mammography, Product Information, Copyright 2010-2014, 1 page.
Hologic, Inc., MammoPad Breast Cushion, Product Information, Copyright 2010, 2 pages.
PCT International Search Report and Written Opinion, PCT/US2015/018473, May 22, 2015, 11 pages.

* cited by examiner

MICROFIBER RADIOGRAPHY COMFORT DEVICE

CROSS-REFERENCE TO RELATED APPLICATION

Not applicable.

STATEMENT OF FEDERALLY SPONSORED RESEARCH OR DEVELOPMENT

Not applicable.

BACKGROUND

This application relates to a radiolucent cover for a medical imaging device such as, for example, a cover for a panel or paddle used in mammography.

Medical imaging has become an increasing powerful diagnostic and screening tool. As one example, breast cancer screening using mammography is routinely performed in order to provide early detection of breast cancer particularly in high-risk and middle-aged populations. If characteristic masses or microcalcifications are identified in the breast tissue during a mammogram, then the matter can be further investigated and, if necessary, treatment may be performed.

Although early detection and treatment of breast cancer greatly improves outcomes, receiving a mammogram is often uncomfortable.

In order to obtain the best resolution for detection of the smallest, earliest cancers, the breast being imaged must be flattened using pressure between two plates or paddles. Discomfort from the pressure can be compounded by the coldness of the paddles. Further, stickiness and pinching can develop when the skin is adjacent to the impermeable surface of the paddle.

Moreover, in order to improve cancer detection, the technician also tries to get as much tissue as possible into the imaging field. This requires uncomfortably driving the chest of the patient into the leading edge of the compressive paddles in an effort to maximize the volume of tissue between the paddles for imaging. However, contact between the patient's chest and the hard leading edge of the paddles results in linear pressure to the patient's rib cage and can be a significant source of pain.

SUMMARY

Discomfort may be an unavoidable part of receiving a mammogram, but excessive pain has the potential to discourage patients from receiving regular mammograms. Disclosed herein is a radiography comfort device that is selectively attachable to the panels or paddles that are used to compress the breast tissue. When attached, this comfort device is able to provide a more pleasant contact surface between the patient's skin and the compression surface of the paddles and, in some forms, is also able to provide better protection against pain from driving the patient's chest and rib cage against the edges of the compression paddles.

A radiography comfort device is disclosed for selective attachment to a panel of a medical imaging device such as, for example, the compressive paddles of a mammography machine. The radiography comfort device includes a woven microfiber fabric and a first adhesive that are radiolucent to X-rays. The woven microfiber fabric has a first surface and a second surface on opposing sides of the woven microfiber fabric. These first and second surfaces are bounded by an outer peripheral edge. The first adhesive is laminated to the second surface of the woven microfiber fabric. When the radiography comfort device is attached to the panel of the medical imaging device using the first adhesive, the first surface of woven microfiber fabric is presented for contact by tissue of an individual being imaged.

In some forms, the radiography comfort device may further include a pad disposed along a portion of the peripheral edge. This pad may be compressible foam or other soft compressible material and, when the comfort device is attached to the panel of the medical imaging device, this pad may be received on a leading edge of the panel to provide comfort against edge pressure. So that the pad does not need to be radiolucent (and potentially more costly to produce), the pad may be disposed at a location that is substantially outside of an area being imaged when the radiography comfort device is attached to the panel.

Consistent with the shape of many panels or paddles, the portion of the peripheral edge along with the pad is disposed may be substantially linear. The pad may be attached to or laminated to the woven microfiber fabric in a number of different ways. In one arrangement, the pad may be adhered to the first surface of the woven microfiber fabric (that is, to the surface opposite to the side of the fabric supporting the first adhesive for attaching the fabric to the panel). In an alternative arrangement, the pad might be adhered to the second surface of the woven microfiber fabric (that is, to the surface that has the adhesive thereon for attaching the fabric to the panel).

In some forms, the first adhesive may be a releasable pressure-sensitive adhesive for adherence and removal to the panel of the medical imaging device. Such a releasable adhesive might be selected to minimize the amount of adhesive residue on the panel. It is contemplated that some or all of the area of the second surface of the fabric might support this first adhesive. For example in some forms, the first adhesive may cover the entire area of the second surface of the woven microfiber fabric. However, in other forms, the first adhesive may only cover a portion of the entire area of the second surface of the woven microfiber fabric. For example, only an area around the perimeter or the corners of the comfort device might support the adhesive to permit the comfort device to be drawn taut without centrally including adhesive on the fabric layer.

Further, it is contemplated that the first adhesive may be laminated directly to the second surface of the woven microfiber fabric with no intermediate layers therebetween. However, it is also contemplated that there could be intermediate layers between the woven microfiber fabric and the first adhesive.

For example, if there are intermediate layers, then the radiography comfort device may include a supporting film having a first surface and a second surface. The first surface of the supporting film may be directly attached to the second surface of the woven microfiber fabric by a second adhesive and the second surface of the supporting film may directly receive the first adhesive. In the above-cited arrangement having an intermediate layer, the first adhesive may be a releasable adhesive for adherence and removal to the panel of the medical imaging device while the second adhesive may be a permanent adhesive forming a substantially irreversible bond between the second surface of the woven microfiber fabric and the first surface of the supporting film. It is contemplated that the supporting film may be sufficiently rigid or stiff to maintain the radiography comfort device in a substantially planar shape during handling of the radiography comfort device and to resist folding. Such a film could also help ensure the device is applied without wrinkling, given that the woven microfiber fabric with only adhesive applied to the fabric may be rather thin and have a tendency to fold onto itself, making application difficult.

In some forms, the radiography comfort device may further include a release liner supporting the first adhesive on a side of the first adhesive opposite to a side of the first adhesive facing the second surface of the woven microfiber fabric. This release liner may be removable from the first adhesive to expose an attachment face of the first adhesive (for later attachment to the surface of the panel) without separating the first adhesive from the second surface of the woven microfiber fabric.

To maintain radiolucence, materials used to form the device should be materials that do not unacceptably impair the imaging of the tissue or the transmission of the electromagnetic waves that perform the imaging. For example, in the woven microfiber fabric, the microfiber threads may be less than 25 microns in diameter, which is below the resolution of X-ray waves (40 to 50 microns). The fibers of the woven microfiber fabric might include, for example, one or more of polyester, polypropylene, polyethylene, and polyurethane. As another example of a material that is radiolucent, the first adhesive may be an acrylic adhesive that is radiolucent to X-rays.

These and still other advantages of the invention will be apparent from the detailed description and drawings. What follows is merely a description of some preferred embodiments of the present invention. To assess the full scope of the invention the claims should be looked to as these preferred embodiments are not intended to be the only embodiments within the scope of the claims.

DETAILED DESCRIPTION

Figure 1:
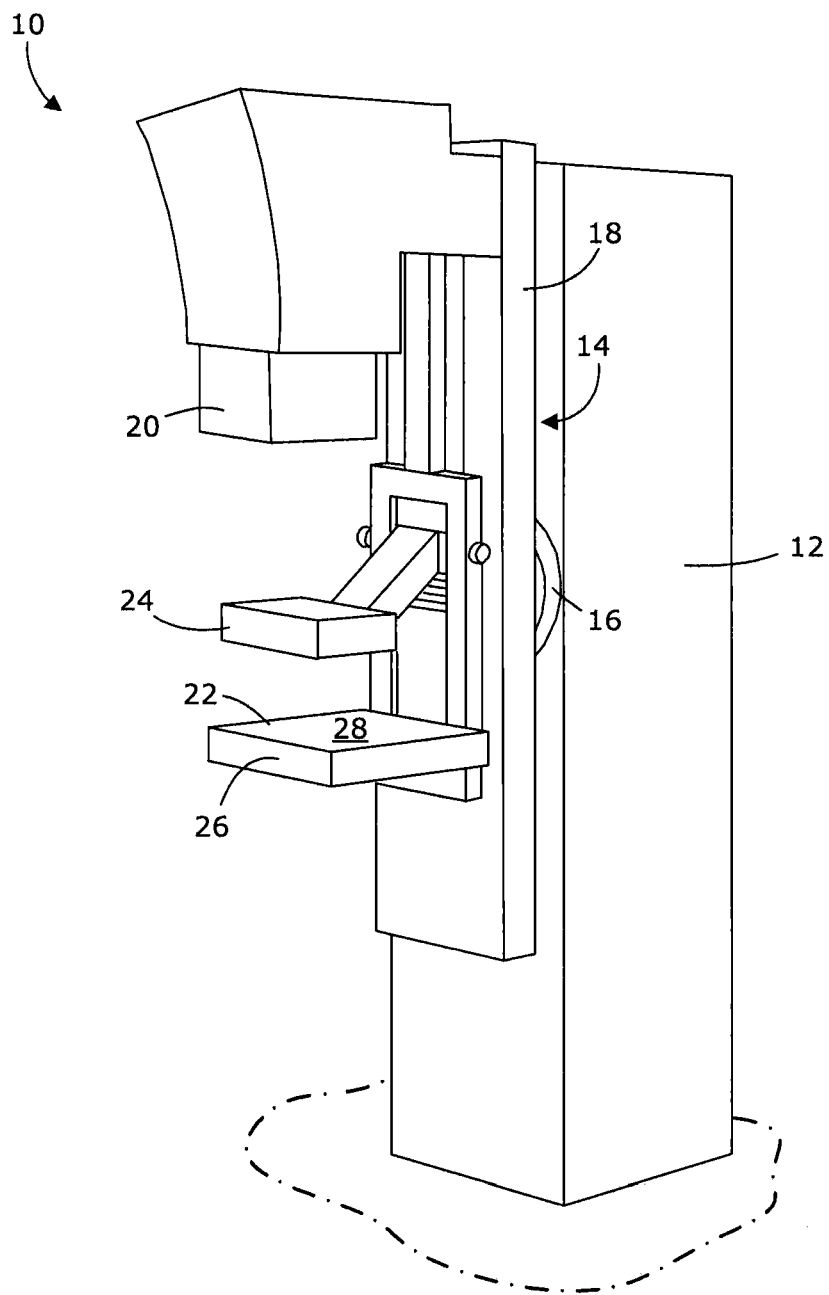
FIG. 1 is a perspective view of an exemplary mammography machine to which the inventive radiography comfort device can be attached.

Referring first to FIG. 1 and to provide some context for the description of the radiography comfort device that follows, an exemplary mammography machine 10 is illustrated. The mammography machine 10 includes a pedestal 12 to which an imaging subassembly 14 is rotatably mounted at a connection joint 16. As illustrated, a rotatable arm 18 of the imaging subassembly 14 is connected to the pedestal 12 and is vertically oriented. This arm 18 supports an X-ray source 20 at a top end thereof, a film table 22 at a lower or central end thereof, and has an adjustable compression paddle 24 disposed between the X-ray source 20 and the film table 22.

In use, the patient stands in front of the machine 10 such that her chest faces the leading edge 26 of the film table 22. The arm 18 is first adjusted to a height and orientation at which the patient's breast tissue can be received on a generally upwardly-facing support surface 28 of the film table 22. With the tissue in place, the compression paddle 24 is lowered and moved toward the film table 22, thereby compressing the breast tissue between the compression paddle 24 and the film table 22 for imaging. At this point, the X-ray source 20 can be operated, transmitting X-rays through the compression paddle 24 (which is radiolucent) and the compressed breast tissue for reception at the film table 22. The film table 22 may have a physical film or (in other forms) may include various sensors that convert the received X-rays into a digital image that can be interpreted for detection of irregularities in tissue.

It will be appreciated that the described mammography machine 10 is only illustrative of the one type of mammography machine. It is contemplated that the radiography comfort devices described herein could be used in other varieties of mammography machine or with other medical imaging devices. Accordingly, nothing in this description should be considered as limiting the application of the inventive comfort device to this single type of exemplary mammography machine.

However, the illustrated mammography machine 10 does highlight some exemplary surfaces to which the radiography comfort devices might be temporarily affixed prior to loading the patient into the machine 10. For example, both the support surface 28 on the film table 22 and the underside of the compression paddle 24 (that is, the side of the compression paddle 24 facing the support surface 28) are skin-contacting surfaces. The radiography comfort device described herein might be applied to one or both of these surfaces in the illustrated machine.

For the sake of simplicity in the description that follows, the term "panel" will be used herein to describe the skin-contacting objects and surfaces of the medical imaging device to which the comfort device might be applied. Accordingly, the term "panel" encompasses structures including compression paddles, film tables or other lower plates in a mammography machine, as well as any other skin contacting surface on a medical imaging device. Conventionally, the surface of the panel will be planar; however, it is contemplated that the surfaces might have some curvature or three-dimensional shape to them.

Figure 2:
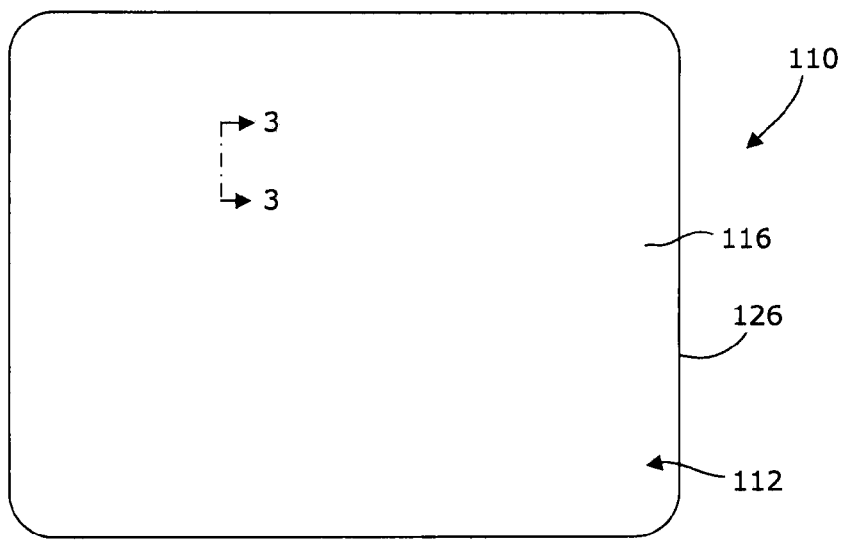
FIG. 2 is a top view of one embodiment of the radiography comfort device.
Figure 3:
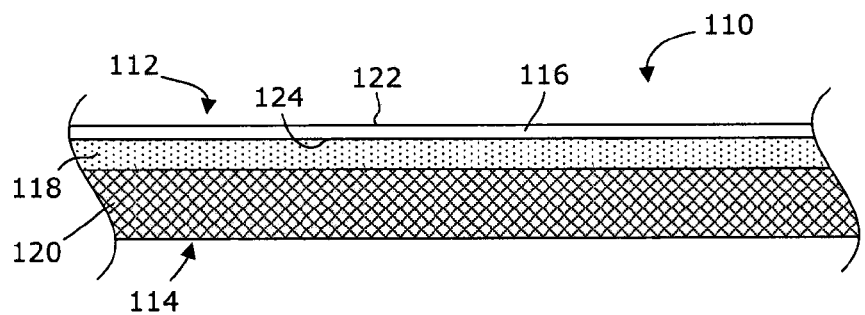
FIG. 3 is a cross section taken through the thickness of the radiography comfort device along line 3-3 of FIG. 2 in which the releasable adhesive is directly laminated to the woven microfiber fabric.

Turning now to FIGS. 2 and 3, a radiography comfort device 110 according to one aspect of the invention is shown. The radiography comfort device 110 is a generally flat rectangular-shaped laminate with rounded corners having a top side 112 and a bottom side 114. As best illustrated in FIG. 3, the radiography comfort device 110 is a laminate including (from the top side 112 to the bottom side 114) a woven microfiber fabric 116, a releasable pressure-sensitive adhesive 118, and a removable release liner 120. The woven microfiber fabric 116 has an upper, first surface 122 and a lower, second surface 124 that are on opposing sides of the woven microfiber fabric 116 and are bound by an outer peripheral edge 126. The adhesive 118, which is initially supported by the release liner 120 on one side of the adhesive 118, is laminated on the other side of the adhesive 118 to the lower, second surface 124 of the woven microfiber fabric 116 to attach the two together.

In the form illustrated in FIG. 3, the releasable pressure-sensitive adhesive 118 is laminated directly to the lower, second surface 124 of the woven microfiber fabric 116 with no intermediate layers between the woven microfiber fabric 116 and the releasable pressure-sensitive adhesive 118. However, as will be described in greater detail below, there may be additional layers between the fabric 116 and the releasable pressure-sensitive adhesive 118 such as illustrated, for example in FIG. 4.

The shape of the radiography comfort device 110 may be shaped similarly to the shape of the surface of the panel to which the radiography comfort device 110 is to be attached. As illustrated in FIG. 2, the shape is generally rectangular with rounded corners.

To apply or attach the radiography comfort device 110 to a panel of a medical imaging device, the release liner 120 is removed from the releasable pressure-sensitive adhesive 118 such that the lower attachment face of the adhesive 118 is exposed without substantially removing the adhesive from the lower, second surface 124 of the woven microfiber fabric 116. This exposed face of the releasable pressure-sensitive adhesive 118 is contacted with the surface of the panel and mild pressure is applied to temporarily attach the comfort device 110 to the panel. This leaves the upper, first surface 122 of the woven microfiber fabric 116 exposed and presented for contact with the skin or tissue of the patent for improved tactile feel and comfort during medical imaging. In this way, the skin of the patient can be contacted with the woven microfiber fabric 116 instead of the uncovered surface of the panel of the medical imaging device. After the imaging is complete, then the comfort device 110 can be removed from the panel by separating the releasable pressure-sensitive adhesive 118 from the surface of the panel, and the used comfort device 110 can be disposed of for sanitary reasons.

It is contemplated that the releasable adhesive 118 might be laminated to the entire area of the lower, second surface 124 of the woven microfabric fiber 116 or only laminated to a portion of the area of the lower, second surface 124 of the woven microfabric fiber 116. For example, the releasable adhesive might only be laminated to a small area (for example, 1 cm) around the outer peripheral edge 126 and not included on the more centrally-disposed areas of the woven microfabric fiber 116. In still another example arrangement, small areas of releasable adhesive might only be laminated in the areas of the corners of the microfiber fabric; in this arrangement, one corner might be applied to the panel first and the fabric pulled taut before attaching the other corners of the fabric to the panel.

Notably, the materials used to make the radiography comfort device are radiolucent to X-rays, at least for the portions of the comfort device that will be located in the field of imaging. Thus, the woven microfiber fabric and the adhesive (as well as an intermediate supporting film and additional adhesive described in the embodiments below) are radiolucent to X-rays. For any components of the comfort device outside of the field of imaging after attachment of the comfort device to the panel (for example, the removed release liner described above or the edge comfort pad and adhesive used to laminate this pad to the fabric described in the embodiment below), these components would not necessarily need to be radiolucent although it would be acceptable if they were.

The woven microfiber fabric 116 is composed of microfiber threads which, by definition, have a diameter of less than 25 microns and are further radiolucent with respect to X-rays. Further, typical imaging resolution is in the range of 40 to 50 microns, and therefore the size of the microfiber threads will not adversely impair image quality. The microfiber threads might include one or more of polyester, polypropylene, polyethylene, polyurethane, and/or other polymeric materials or blends, for example. It is stressed that the microfiber fabric 116 is a woven material and thus provides improved tactile feel and comfort when contacted by the skin of a user in comparison to a non-woven material. In one particular form, the woven microfiber fabric includes warp and weft yarns at right angles to one another that are woven together using a loom or other textile producing device. It is contemplated that only a single ply of the woven microfiber fabric 116 may be present in the comfort device 110 in order to provide the desired texture and feel; however, it is also contemplated that more than one ply of the woven microfiber fabric might be stitched together or otherwise connected and incorporated into the comfort device 110. The woven microfiber fabric 116 may be substantially non-compressible and its dimensions and relative non-compressibility may not significantly alter the pressure applied to any tissue being compressed for imaging.

The adhesive 118 is used to attach the woven microfiber fabric 116 to the surface of the panel should likewise be radiolucent to X-rays. In one particular form, the adhesive 118 may be an acrylic adhesive, although other adhesives radiolucent to X-rays may also be used.

Other variations may be made to the embodiment shown in FIGS. 2 and 3 described above. For the sake of simplicity in describing similar elements in these variations and to avoid duplication of description, similar reference numerals above "100" will be used hereafter to indicate similar elements having similar qualities and the description of each of these elements are similar to those described elsewhere in this detailed description unless otherwise noted. For example, the woven microfiber fabric 116 in the embodiment illustrated in FIGS. 2 and 3 corresponds to the woven microfiber fabric 216 in the embodiment in FIG. 4, the woven microfiber fabric 316 in the embodiment in FIGS. 5, 6, and 7, the woven microfiber fabric 416 in the embodiment in FIG. 8, and the woven microfiber fabric 516 in the embodiment in FIG. 9.

One of ordinary skill in the art will appreciate that the variations described herein may be made independent of one another or may be made in combination with one another, regardless of whether or not such combination is illustrated. Further, such combinations or modifications workable to result in such combinations are contemplated as falling within the scope of this disclosure.

Figure 4:
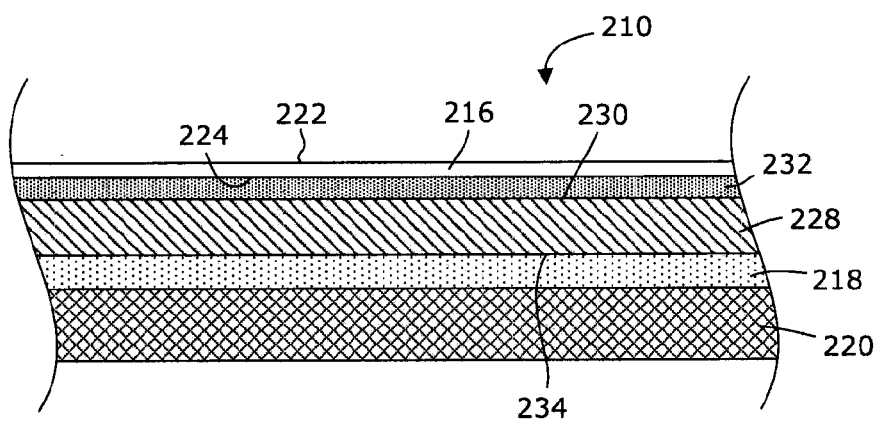
FIG. 4 is a cross section taken through the thickness of another embodiment of the radiography comfort device in which there is an intermediate supporting film that, on one side, has an adhesive that bonds the woven microfiber fabric to the supporting film and, on the other side, receives the releasable adhesive.

In one potential variation to the embodiment illustrated in FIGS. 2 and 3, intermediate layers may be disposed between the woven microfiber fabric 116 and the adhesive 118. With additional reference to FIG. 4, a different layer structure is illustrated in a radiography comfort device 210 in which additional layers are interposed between the woven microfiber fabric 216 and the first, releasable pressure-sensitive adhesive 218. In FIG. 4, one such additional layer is a supporting film 228 disposed between the woven microfiber fabric 116 and the adhesive 118. The supporting film 228 has an upper, first surface 230 that is directly attached to the lower, second surface 224 of the woven microfiber fabric 216 by a second adhesive 232. Meanwhile, a second, lower surface 234 of the supporting film 223 directly receives the first adhesive 218.

There are many potential benefits to these additional layers.

First, the supporting film 228 may be a polymeric film made of a material and having a thickness to provide sufficient rigidity of the comfort device 210 to maintain the radiography comfort device 210 in a substantially planar shape during handling of the radiography comfort device 210. Among other things, maintaining a substantially planar shape (or permitting only a minimal amount of bending) can make it such that the radiography comfort device 210 resists folding, thereby avoiding the adherence of the first adhesive 118, 218 to itself once the release liner 120, 220 is removed. Further, the additional rigidity may aid a technician in placing and adhering the radiography comfort device 210 on a panel, as the comfort device 210 is substantially held in form.

Another benefit may be that the first adhesive 218 and the second adhesive 232 may be selected to have different qualities based on their use in the laminate. For example, as described above, the first adhesive 218 may be a releasable adhesive for adherence and removal to the panel of the medical imaging device. However, such a releasable adhesive might not bond as well as desired to the woven microfiber fabric 216. Accordingly, the second adhesive 232 may be a permanent adhesive forming a substantially irreversible bond between the lower, second surface 224 of the woven microfiber fabric 216 and the upper, first surface 230 of the supporting film 228.

In other variations, a comfort pad may be attached to a portion of the periphery of the radiography comfort device in order to better protect and cushion the patient from a leading edge 26 of a panel 22 while at the same time attaching the woven microfiber fabric to a support surface 28 of the panel 22. The comfort pad may be, for example, a compressible foam such as a polymeric foam, or another type of soft, cushioning material. As noted above, because the edge comfort pad will be outside of the field of imaging, the material of the comfort pad can be radiopaque and not radiolucent as the primary function of this pad is to cushion the patient against the leading edge. This can save substantial cost, because the materials for making the pad are not limited by their ability to be radiolucent.

Figure 5:
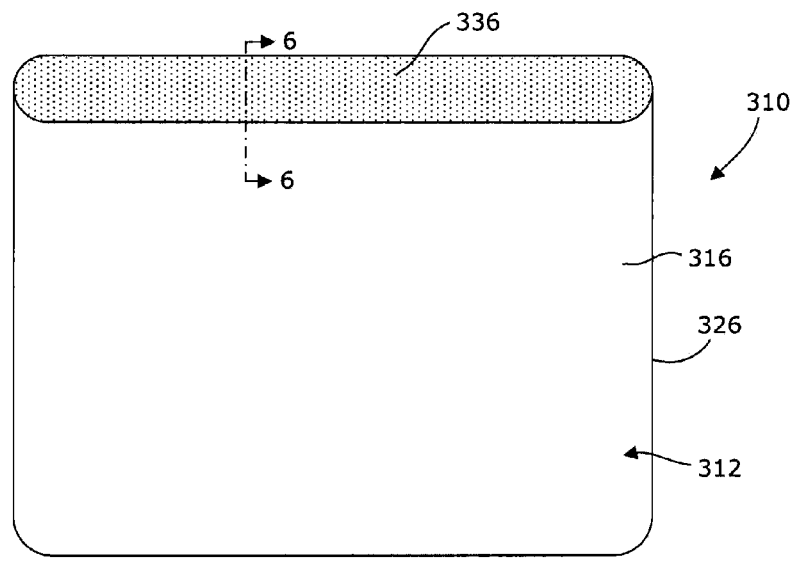
FIG. 5 is a top view of an embodiment of the radiography comfort device in which a comfort pad is adhered to the upper surface of the woven microfiber fabric.
Figure 6:
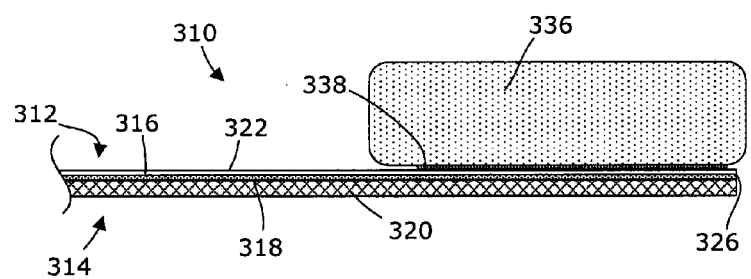
FIG. 6 is a cross-sectional side view taken through line 6-6 of FIG. 5 in which the adherence of the pad to the top surface of the woven microfiber fabric is shown.

With reference to FIGS. 5 and 6, one embodiment of a radiography comfort device 310 is illustrated in which a comfort pad 336 is attached or laminated along one of the peripheral edges 326 of the radiography comfort device 310 on the first, upper surface 322 of the woven microfiber fabric 316 using an additional adhesive 338. In this embodiment, the pad 336 is elongate in shape with a generally rectangular cross section and curved edges and corners. The pad 336 is disposed along only a portion of the peripheral edge 326, which is substantially linear.

Figure 7:
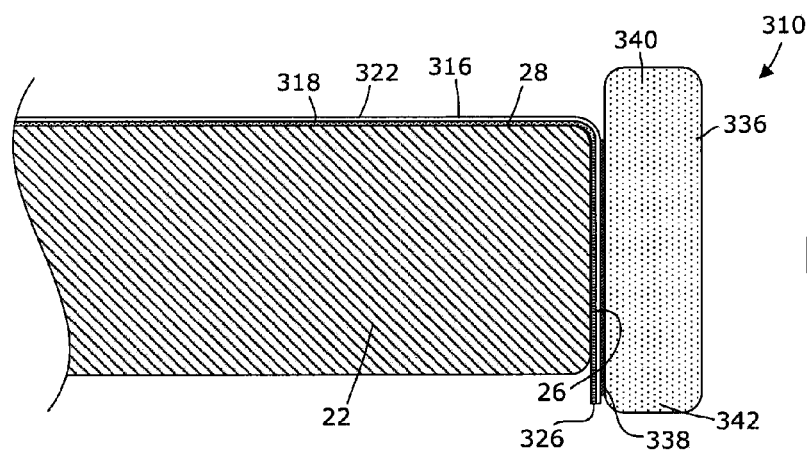
FIG. 7 is a cross-sectional side view of the radiography comfort device from FIG. 6 in which the radiography comfort device is attached to a panel of a medical imaging device such that the pad is positioned over a leading edge of the panel to provide a comfort cushion.

When the radiography comfort device 310 is adhered to a support surface 28 of a panel 22 after the release liner 320 is removed, such as is illustrated in FIG. 7, a portion of the comfort device 310 may drape over the leading edge 26 such that the pad 336 is positioned to protect the user from the leading edge 26. In this regard, the comfort pad 336 may be slightly oversized such that the top part 340 and bottom part 342 of the pad 336 may be above and below the horizontal surfaces of the panel 24. Accordingly, when a pressure is applied by the user to the pad 336, a central portion of the pad 336 deforms and the top part 340 and the bottom part 342 of the comfort pad 336 continue to protect the user from the linear contact between the chest of the patient and line at which the upper and lower horizontal surfaces (e.g., support surface 28) and the leading edge 26 of the panel 24 meet.

Figure 8:
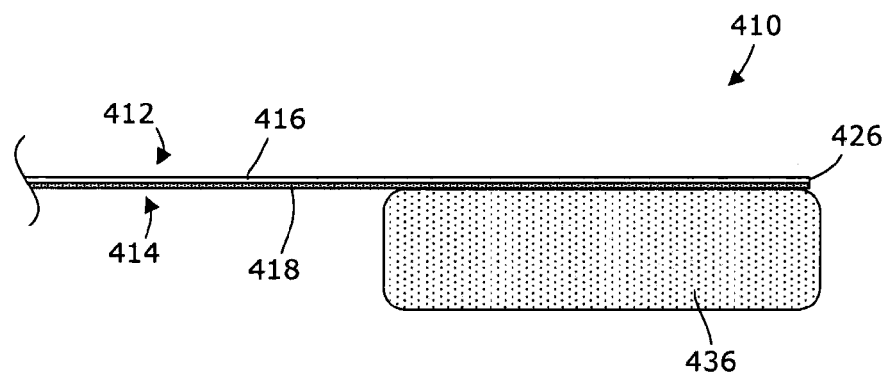
FIG. 8 is another embodiment of a radiography comfort device in which the pad is adhered to a bottom side of the radiography comfort device.

In an alternative form illustrated in FIG. 8, a similarly-shaped comfort pad 436 to comfort pad 336 is shown attached to the bottom side 414 of a radiography comfort device 410 (e.g., laminated or adhered to the lower, second surface 424 of the woven microfiber fabric 416). In the form illustrated in FIG. 8, this is done using the same adhesive 418 that is used to attach the woven microfiber fabric 416 to a panel; however a second area of different type of adhesive might be used instead. In this form, placement of the radiography comfort device 410 onto the panel during adherence might be carefully controlled to permit the pad 436 to drape over and cover a portion of the leading edge by leaving some excess fabric material 416 past the leading edge. Alternatively, the pad 436 might be rotated 90 degrees clockwise on the page relative to the view of the illustration in FIG. 8 to permit the leftmost edge of the pad to adhere to the adhesive 418; then the pad 436 might be gently contacted to the leading edge of the panel as a guide for the placement of the remainder of the planar fabric portion of the comfort device 410 on the panel.

Figure 9:
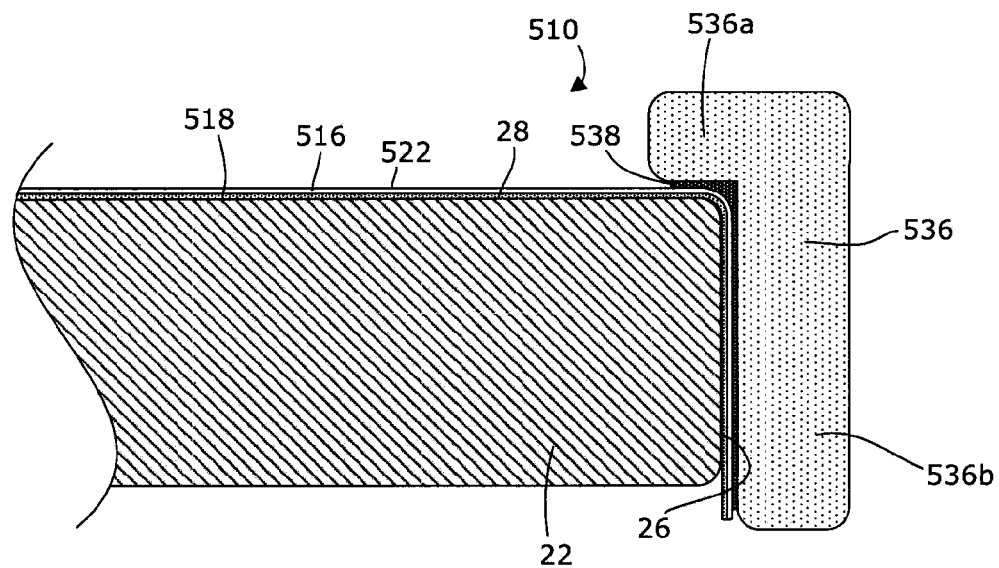
FIG. 9 is yet another embodiment of a radiography comfort device in which the pad is L-shaped to better cover the upper edge of the panel of the medical imaging device.

In FIG. 9, an alternative form is illustrated in which the comfort pad 536 is L-shaped and is laminated to the upper, first surface 522 of the woven microfiber fabric 516. As with the embodiment illustrated in FIGS. 5 through 7, a second adhesive 538 is used to bond or laminate the comfort pad 536 to the woven microfiber fabric 516. Again, this second adhesive 538 may be selected to provide a permanent adhesive bond between the woven microfiber fabric 516 and the comfort pad 536. The L-shaped comfort pad 536 includes a horizontal leg 536a and a vertical leg 536b that meet at a bend (the horizontal and vertical orientations being defined with respect to a horizontally extending panel 22).

As can be seen in FIG. 9, when the radiography comfort device 510 is attached to the panel 22, the comfort pad 536 wraps around the leading edge 26 to the upper support surface 28 of the panel 22. In this way, the horizontal leg 536a covers a portion of the upper support surface while the vertical leg 536b covers the vertically-oriented surface of the leading edge 26. This helps to more effectively protect the user from contact with this upper edge of the panel 22.

Again, it should be stressed that, while a number of variations are illustrated in the figures and described herein, that combinations and further modifications might be made to the exemplary embodiments without departing from the spirit of the invention.

For example, a radiography comfort device might be designed to include both a comfort pad (as in any of FIGS. 5 through 9 or in other forms) as well as to include a supporting intermediate film as in FIG. 4. In such a combination, it will be appreciated that the supporting film may only extend over a portion of the area of the woven microfiber fabric to provide additional rigidity and stiffness, while the portion of the woven microfiber fabric laminated to the comfort pad may remain flexible relative to the portion with the supporting film that will attach to and cover the upper surface of the panel such that the comfort pad can wrap over and cover the leading edge.

As another example, it will be appreciated that the comfort pad could be formed with a different geometry relative to those illustrated. For example, the comfort pad could have a C-shaped geometry that wraps over the upper and lower portions of the leading edge. In such a comfort device, it is contemplated that the comfort pad portion of the comfort device might first be hooked on the leading edge to position the device and, then, the adhesive laminated to the underside of the woven microfiber fabric may be adhered to the support surface of the panel such that the area of contact between the leading edge and the pad serves as a datum.

Further, it should be appreciated that, while the embodiments illustrated in FIGS. 7 and 9 show the woven microfiber fabric and adhesive wrapping over the leading edge, it is not necessary for them to do so or, even if the woven microfiber fabric does wrap over the edge, then it may not be adhered to the leading edge via the pressure sensitive adhesive. It is contemplated that a comfort pad might be laminated to the woven microfiber fabric on the upper surface of the fabric, that this fabric and adhesive may be arranged for attachment only to an upper support surface of the panel, and that a portion of the comfort pad may extend over, down, and past the leading edge. Indeed, from a production perspective, it may be easier to produce a comfort device of this type because, unlike the illustrated embodiment of FIG. 9, only one planar surface of the pad would be laminated to the woven microfiber fabric instead of the two perpendicular surfaces of the pad as illustrated.

Finally, it is worth taking a moment to describe a general process for producing the structures described above, observing that the process described below is not the only process for fabricating the radiography comfort devices and that other processes or variations to the process might be used.

To make the radiography comfort device, a release liner may initially be provided and adhesive may be applied to the release liner by, for example, spraying or rolling the adhesive onto the release liner. Then, if it is desired, the supporting film may be laminated to the adhesive coated side of the release liner and another adhesive applied to the exposed surface of the supporting film. A woven microfiber fabric is then laminated to either the adhesive-coated release liner or, if they are present, the adhesive on the supporting film. Because it is likely most economical to perform this operation on continuous rolls of material, the radiography comfort device might be cut (for example, die cut) from the resultant laminate to have the desired outer periphery and shape for the panel to which it is to be attached. In order to attach a comfort pad, separate adhesive-applying steps and/or laminating steps may occur. Then, typically, the comfort devices will be packaged in sealed packaging to ensure that they remain clean or sterile for patient use. Of course, it should be appreciated that while the above-described process is generally illustrative, it is in no way limiting.

Thus, a radiography comfort device is disclosed that can reduce the discomfort associated, with medical imaging procedures such as mammography. The woven microfiber fabric of the material may provide an improved tactile feel to the support surface while an attached comfort pad can reduce the pain of edge pressure on the rib cage or the chest of the patient. Moreover, this comfort can be provided without impairing the quality of the resultant radiological image as radiolucent materials are used in the field of imaging, while permitting the use of less-costly radiopaque materials outside of the field of imaging to achieve, for example, edge protection using the comfort pad.

It should be appreciated that various other modifications and variations to the preferred embodiments can be made within the spirit and scope of the invention. Therefore, the invention should not be limited to the described embodiments. To ascertain the full scope of the invention, the following claims should be referenced.

What is claimed is:

1. A radiography comfort device for selective attachment to a panel of a medical imaging device, the radiography comfort device comprising:
   a woven microfiber fabric having a first surface and a second surface on opposing sides of the woven microfiber fabric, the first surface and the second surface bounded by an outer peripheral edge; and
   a first adhesive laminated to the second surface of the woven microfiber fabric;
   wherein the woven microfiber fabric and the first adhesive are radiolucent and, when the radiography comfort device is attached to the panel of the medical imaging device using the first adhesive, the first surface of woven microfiber fabric is presented for contact by tissue of an individual being imaged.

2. The radiography comfort device of claim 1, further comprising a pad disposed along a portion of the peripheral edge wherein the pad is adapted to be received on an edge of the panel of the medical imaging device.

3. The radiography comfort device of claim 2, wherein the portion of the peripheral edge along with the pad is disposed is substantially linear.

4. The radiography comfort device of claim 2, wherein the pad is adhered to the first surface of the woven microfiber fabric.

5. The radiography comfort device of claim 2, wherein the pad is adhered to the second surface of the woven microfiber fabric.

6. The radiography comfort device of claim 2, wherein the pad comprises compressible foam.

7. The radiography comfort device of claim 2, wherein the pad is laminated to the woven microfiber fabric.

8. The radiography comfort device of claim 2, wherein the pad is disposed at a location that is substantially outside of an area being imaged when the radiography comfort device is attached to the panel.

9. The radiography comfort device of claim 1, wherein the first adhesive is a releasable pressure-sensitive adhesive for adherence and removal to the panel of the medical imaging device.

10. The radiography comfort device of claim 1, wherein the first adhesive is laminated directly to the second surface of the woven microfiber fabric with no intermediate layers therebetween.

11. The radiography comfort device of claim 1, further comprising a supporting film having a first surface and a second surface, the first surface of the supporting film being directly attached to the second surface of the woven microfiber fabric by a second adhesive and the second surface of the supporting film directly receiving the first adhesive.

12. The radiography comfort device of claim 11, wherein the first adhesive is a releasable adhesive for adherence and removal to the panel of the medical imaging device and the second adhesive is a permanent adhesive forming a substantially irreversible bond between the second surface of the woven microfiber fabric and the first surface of the supporting film.

13. The radiography comfort device of claim 11, wherein the supporting film is sufficiently rigid to maintain the radiography comfort device in a substantially planar shape during handling of the radiography comfort device and resist folding.

14. The radiography comfort device of claim 1, further comprising a release liner supporting the first adhesive on a side of the first adhesive opposite to a side of the first adhesive facing the second surface of the woven microfiber fabric.

15. The radiography comfort device of claim 14, wherein the release liner is removable from the first adhesive to expose an attachment face of the first adhesive without separating the first adhesive from the second surface of the woven microfiber fabric.

16. The radiography comfort device of claim 1, wherein the diameter of the microfiber threads in the woven microfiber fabric are less than 25 microns in diameter.

17. The radiography comfort device of claim 1, wherein the first adhesive is an acrylic adhesive that is radiolucent to X-rays.

18. The radiography comfort device of claim 1, wherein the fibers of the woven microfiber fabric comprise at least one of polyester, polypropylene, polyethylene, and polyurethane.

19. The radiography comfort device of claim 1, wherein the first adhesive covers an entire area of the second surface of the woven microfiber fabric.

20. The radiography comfort device of claim 1, wherein the first adhesive covers only a portion of the entire area of the second surface of the woven microfiber fabric.

* * * * *